(12) United States Patent
Bittner

(10) Patent No.: US 7,094,562 B2
(45) Date of Patent: Aug. 22, 2006

(54) METHOD FOR THE EXAMINATION OF CELLS IN A CULTURE MEDIUM

(75) Inventor: Christoph Bittner, Hemel Hempstead (GB)

(73) Assignee: Innovatis AG, (DE)

( * ) Notice: Subject to any disclaimer, the term of this patent is extended or adjusted under 35 U.S.C. 154(b) by 521 days.

(21) Appl. No.: 10/332,303

(22) PCT Filed: Jul. 7, 2001

(86) PCT No.: PCT/EP01/07814

§ 371 (c)(1),
(2), (4) Date: Jun. 26, 2003

(87) PCT Pub. No.: WO02/04924

PCT Pub. Date: Jan. 17, 2002

(65) Prior Publication Data

US 2004/0048330 A1    Mar. 11, 2004

(30) Foreign Application Priority Data

Jul. 10, 2000    (DE) ............................... 100 33 268

(51) Int. Cl.
*G01N 33/487*  (2006.01)
*G06K 9/00*  (2006.01)

(52) U.S. Cl. ..................................... 435/40.5; 382/128
(58) Field of Classification Search ............... 435/40.5; 382/128

See application file for complete search history.

(56) References Cited

U.S. PATENT DOCUMENTS

| | | |
|---|---|---|
| 2,850,239 A | 9/1958 | Polanyi |
| 4,245,914 A | 1/1981 | Clack |
| 4,776,697 A | 10/1988 | Kamrat |
| 5,188,968 A | 2/1993 | Kano |

FOREIGN PATENT DOCUMENTS

| EP | 0 391 674 A2 | 10/1990 |
| WO | WO 99/35496 A1 | 7/1999 |
| WO | WO 99/44593 A1 | 9/1999 |

OTHER PUBLICATIONS

Burmeister, J.S., Application of Total Internal Reflection Fluorescence Microscopy to Study Cell Adhesion to Biomaterials, Biomaterials (1998), vol. 19, pp. 307-325.
Ramic, A.J., Temporary Droplet-Size Hysteresis in Immiscible Polymer Blends, Polymer (2000), vol. 41, pp. 6263-6270.
Kreysa, G. (editor), Microbial Principles in Bioprocesses Cell Culture Technology Downstream Processing and Recovery, Dechema Biotechnology Conferences (1992) vol. 5, Part A.
Suhr, H., In Situ Microscopy for On-Line Characterization of Cell-Populations in Bioreactors, Including Cell-Concentration Measurements by Depth from Focus, Biotechnology and Bioengineering (1995), vol. 47, pp. 106-116.
Bittner, C., In Situ Microscopy for On-Line Determination of Biomass, Biotechnology and Bioengineering (1998), vol. 60, No. 1, pp. 24-35.
German Patent Office Search Report on priority application.

*Primary Examiner*—Ralph Gitomer
*Assistant Examiner*—Kailash C. Srivastava
(74) *Attorney, Agent, or Firm*—Powell Goldstein LLP; Laurence P. Colton

(57) ABSTRACT

The invention relates to a method for the examination of cells (20, 38) in a culture medium, in particular for in-situ microscopy in a bio-reactor, whereby cells in a sample volume, the depth (d) of which is defined by windows (14, 16) in the direction of the optical axis of the microscope (18), are microscopically imaged and are automatically recorded and processed by means of an image processing system (30). Said method is characterized in that the depth (d) of the sample volume (12) is adjusted to the size of the cells (20, 38) by successively reducing the separation (d) of the windows while the image size (G) of the cells is simultaneously verified by the image processing system (30) such that a separation value (D) is determined at which the image size (G) of the cells begins to grow, thus corresponding to flattening caused by the contact pressure of the windows (14, 16), and that the separation (d) of the windows (14, 16) is set to said separation value (D) for the examination.

17 Claims, 7 Drawing Sheets

METHOD FOR THE EXAMINATION OF CELLS IN A CULTURE MEDIUM

BACKGROUND OF THE INVENTION

1. Technical Field

The invention relates to a method for the examination of cells in a culture medium, in particular for in-situ microscopy in a bio-reactor, whereby cells in a sample volume, the depth of which is defined by windows in the direction of the optical axis of the microscope, are microscopically imaged and are automatically recorded and processed by means of an image processing system, and to an apparatus for implementing this method.

2. Prior Art

Such a method is disclosed by DE 40 23 002 C2, for example, and is particularly advantageous for use in bio-reactors which are also used for the cultivation of cells on an industrial scale. The automatic regulation of cell cultivation processes in the reactor requires measured values which provide information about the state of the culture medium. In principle, this method is not limited to organic cells but can also be used for the examination of other, inorganic particles in a medium, such as in an oil suspension or the like. For this reason, the term "cell" should be understood in its broadest sense, although reference will be made in the following to organic cells.

In the known method, the cells are imaged microscopically, with the image being captured by an automatic image processing system. The examined sample volume is defined in the direction of the optical axis of the microscope by windows, which ensure an unimpeded view of the sample volume.

Of special interest is the concentration, size and morphology of the cells. Furthermore, with in-situ microscopy it is possible to determine the cell size distribution, thus providing information for determining the anhydrous bio-mass. These parameters are supplied immediately by the described method, whereas offline analytic methods requiring the manual taking of samples are not suited for achieving a satisfactory regulation of the cell cultivation process.

However, it has proved difficult to obtain detailed information on the cell population in a bio-reactor because of the constraints imposed by the image processing system in recording all cells in the sample volume reliably. In order to examine as many cells as possible, the selected value for the distance between the windows and thus the depth of the sample volume must be as large as possible. This in turn is problematical, since the limited depth of field of the lens allows for only a narrow field of clear focus, and thus only a small number of cells can be imaged in clear detail and recorded by the image processing system in each measuring cycle. It is also difficult to differentiate individual cells when cells floating in suspension block each other from view. To insure that the image can be properly evaluated, it is necessary to use image processing software that is very expensive but does not always yield reliable results. In addition, some examination methods may require longer exposure times when imaging the cells. But this is not possible if the cells are able to move about freely in the sample volume.

On the other hand, if the sample volume is narrowed along the optical axis to a point where its thickness corresponds to the depth of field of the microscope lens, this results in very few cells being present within the sample volume for examination. If the sample volume is very narrow, this will also prevent an unimpeded flow of the culture medium between the windows.

BRIEF SUMMARY OF THE INVENTION

The object of the invention is therefore to present a method of the type introduced above which makes it possible to record and process a relatively large number of cells during one measuring cycle while avoiding the problems described above, and an apparatus for implementing this method.

This object is solved by the invention pursuant to a method for the examination of cells in a culture medium, in particular for in-situ microscopy in a bio-reactor, whereby cells in a sample volume, the depth (d) of which is defined by windows in the direction of the optical axis of the microscope, are microscopically imaged and are automatically recorded and processed by means of an image processing system, characterized in that the depth (d) of the sample volume is adjusted to the size of the cells by successively reducing the separation (d) of the windows while the image size (G) of the cells is simultaneously verified by the image processing system such that a separation value (D) is determined at which the image size (G) of the cells begins to grow, thus corresponding to flattening caused by the contact pressure of the windows, and that the separation (d) of the windows is set to said separation value (D) for the examination and an apparatus for the examination of cells in a culture medium, in particular for in-situ microscopy in a bio-reactor, with a microscope for the imaging of cells within a sample volume, the depth (d) of which is defined by windows in the direction of the optical axis of the microscope, and an image processing system for recording and processing the microscope image, characterized by an actuator for adjusting the separation (d) between the windows of the sample volume along the optical axis which can be controlled by the image processing system by means of a control unit such that the separation (d) between the windows can be set for the examination to a separation value (D) at which point the image size (G) of the cells starts to grow in accordance with their flattening caused by the contact pressure of the windows.

In the method according to the invention relating to in-situ microscopy, the depth of the sample volume is adjusted to the size of the cells to be examined such that the separation of the windows is gradually reduced while the image size of the cells is monitored by the image processing system. If the window separation becomes so small that the windows touch the cells on both sides, the cells are compressed and flattened and consequently their image size starts to grow at this point. This increase in the image size is registered by the image processing system and the separation of the windows is set at a constant separation value marking the point where the image size starts to increase due to cell flattening.

At this separation value the windows contact the cells in the sample volume at both sides, thereby exerting a slight clamping pressure on the cells such that the thickness of the sample volume corresponds approximately to the cell thickness. In this manner the sample volume can be made very small while containing a relatively large number of cells that can be examined. All of these cells are located in an object level perpendicular to the optical axis of the microscope and within its depth of field, so that all cells can be imaged well. Furthermore, this avoids any superimposition of the cells and makes it possible to identify all cells individually. Since the cells can be maintained in this position between the windows, it is possible to make images requiring longer exposure times, should this prove necessary.

Due to the risk of cell damage occurring when the windows are brought together, this procedure must be executed with the greatest of precision. If a flattening of the cells is registered, the window separation distance is reverted to the last value recorded before cell flattening initiated. Examination of the cells is then conducted at this point.

If the culture medium contains cells of different size, they can be classified according to size by means of the image processing system such that only cells of a selected size group are used for determining the thickness of the sample volume. This means that the window separation distance is set to a constant value, as described above, at the point where the image size of the cells in this size category starts to increase. Here the image size or cell flattening is not taken into account. If, for example the thickness of the sample volume is set to correspond to the largest cells, no flattening occurs in the other cells when the window separation distance is decreased and they assume relatively free locations in the sample volume. If the window separation is set to correspond to smaller cells, the larger cells are destroyed when the windows are moved to this smaller separation distance. The images of these destroyed cells can be identified by the image processing system and ignored during examination, so that only the smaller cells are analyzed.

Furthermore, it is preferably possible to examine cells which adhere to platelet-shaped carriers. These carriers, which float freely in the culture medium, are polystyrene platelets having a diameter of approximately 0.1 mm and a thickness of 20 µm. These carriers bear suction cells, for example, which tend to colonize flat surfaces. The cells adhering to the carriers can be easily observed by moving the windows of the sample volume together in the manner according to the invention. During this procedure the carriers assume a flat position between the windows. By observing the image size of the cells located on one side of a carrier, for example the side facing the microscope lens, it is possible to decrease the separation of the windows in the described manner until a flattening of the imaged cells commences. The set measuring distance thus corresponds to the approximate thickness of the carrier plus the double row of cells diameters. During this process, the image level of the microscope is preferably shifted to the cell layer to be examined and its depth of field limited to a point where only cells in this layer are in focus. The cells on the opposite surface side of the carrier are thus not imaged, thus avoiding any problems in the image processing system caused by superimposed images of overlapping cells. The depth of field can be shifted between the two cell layers on either side of the carrier so that all cells in the sample volume can be observed separately.

The field of depth of the microscope lens can be preferably adjusted by altering the numeric aperture of the microscope lens, for example by means of a diaphragm.

Due to the greater degree of precision required for determining the separation distance, it is relatively time-consuming to determine the separation at the start of each new measuring cycle. Therefore, it is preferred to store in a measuring cycle the separation value for a particular cell type, which can be retrieved in subsequent measuring cycles and thus the window separation distance can be set immediately to the stored value.

If the culture medium contains carriers with adherent cells as well as free-floating cells, the image processing system preferably decides whether a carrier or cells are present in the sample volume in order that it can select the corresponding window separation. For example, if a carrier is present in the sample space, a pre-determined separation value for the carrier is retrieved and the thickness is set to the appropriate value. Likewise, the thickness is adapted to a cell inasmuch as only cells are present in the sample space. Preferably, at least one of the windows is cleaned by a wiper either before or after the measuring process in order to remove cells clinging to the transparent surfaces.

An apparatus for implementing the method according to the invention also is disclosed, along with advantageous embodiments of this apparatus.

BRIEF DESCRIPTION OF THE DRAWINGS

In the following, a preferred exemplary embodiment of the invention will be discussed in detail with reference being made to the drawings, which show.

DETAILED DESCRIPTION OF THE PREFERRED EMBODIMENTS

Figure 1:
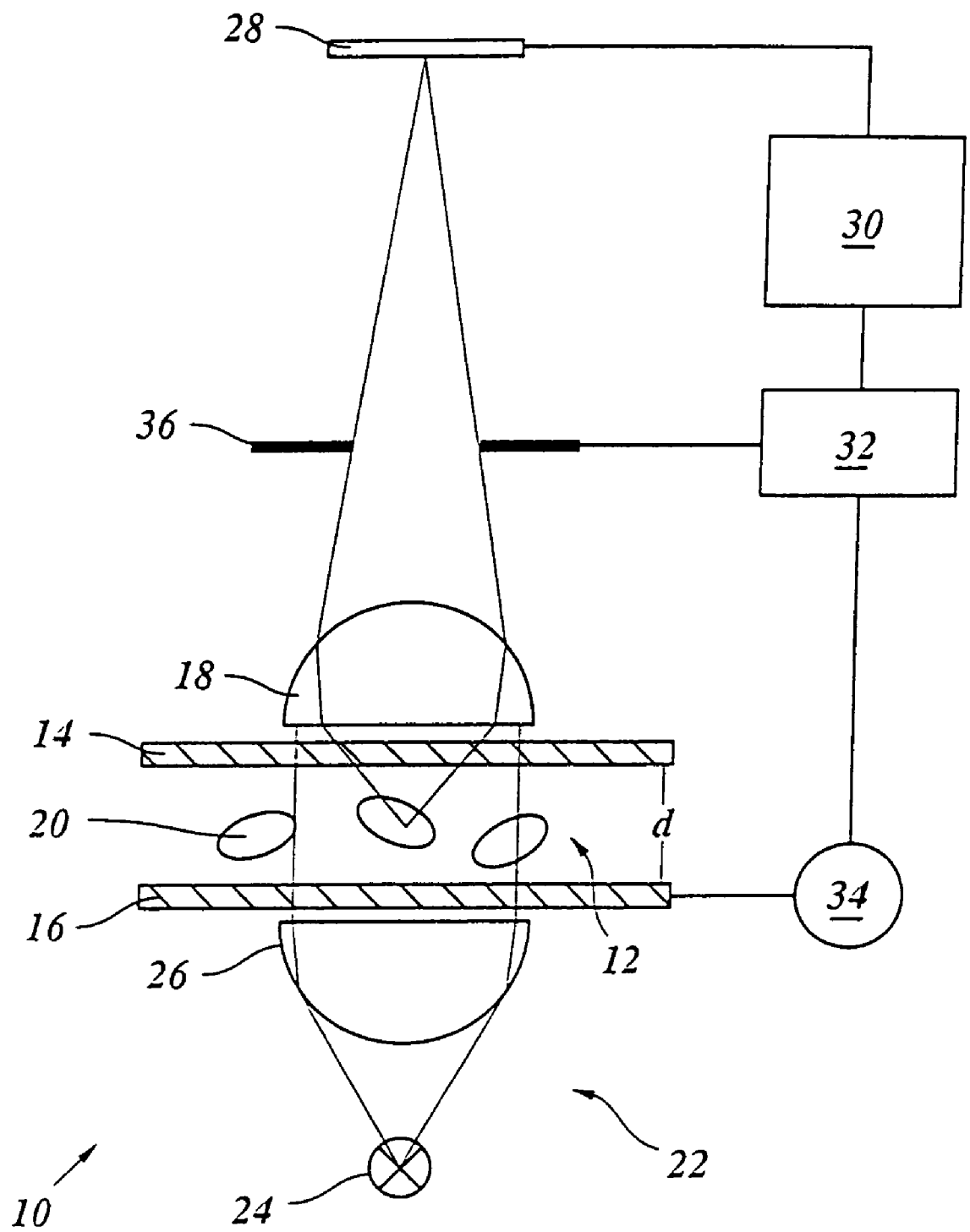
FIG. 1 illustrate a schematic representation of an embodiment of an apparatus for implementing the method according to the invention.

The apparatus 10 shown in FIG. 1 for in-situ microscopy of cells in a culture medium encompasses a sample volume 12 between two windows 14, 16 that are aligned perpendicular to the optical axis of a microscope lens 18 used to image cells 20 in the sample volume 12. In the most simple embodiment, the windows 14, 16 are glass plates. The embodiment shown here serves primarily for examining organic cells 20. But in principle the present invention is not limited to such cells but is also suited for examining non-organic particles suspended in a liquid medium.

The sample volume 12 is illuminated by an illumination arrangement 22 having a light source 24 and a condenser 26 operating in a so-called transmitted-light mode. In the case shown here, a bright-field illumination is employed, but any other type of illumination arrangement is also possible. If the illumination source and the lens 18 are located on the same side of the object, as is the case in an incident-light arrangement, the opposite window does not necessarily have to be transparent but in principle can also be an opaque rear wall of the sample chamber.

The microscope lens 18 images the cells 20 on an electronic image sensor 28 connected to the image processing system 30 used for the electronic recording and processing of the image. Furthermore, the image processing system 30 is also connected to a control unit 32 for controlling an actuator 34 which effects a linear shift of the window 16 of the sample volume 12 facing away from the microscope lens 18. The depth d of the sample volume 12 in the direction of the optical axis can thus be altered by the actuator 34. In addition, an adjustable diaphragm 36, which can also be addressed by the control unit 32, is arranged between the microscope lens 18 and the image sensor 28.

The depth of field of the lens 18 is determined by its numeric aperture. A high numeric aperture value results in a low depth of field, i.e. only a narrow range of the sample volume 12 is imaged in focus. The numeric aperture can be changed by either opening or closing the diaphragm 36. In order to image a large number of cells 20 in the sample volume in sharp focus, prior to analysis, the thickness d is gradually decreased until all cells 20 lie in a single layer between the windows 14, 16.

Figure 2:
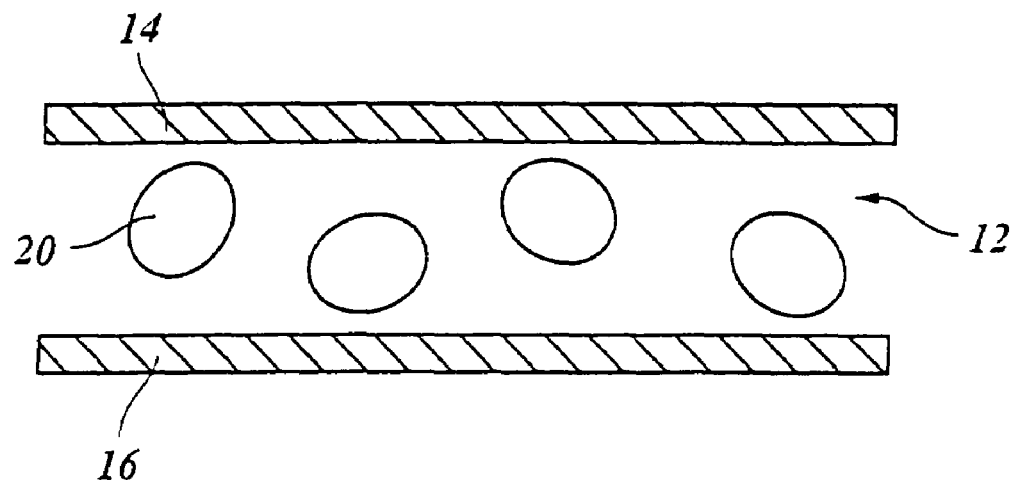
FIGS. 2 to 4 illustrate detailed views of the sample volume of the apparatus in FIG. 1.
Figure 3:
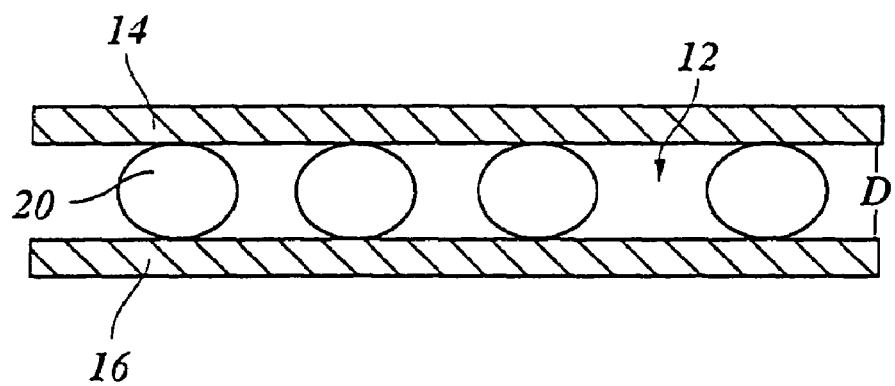
Figure 4:
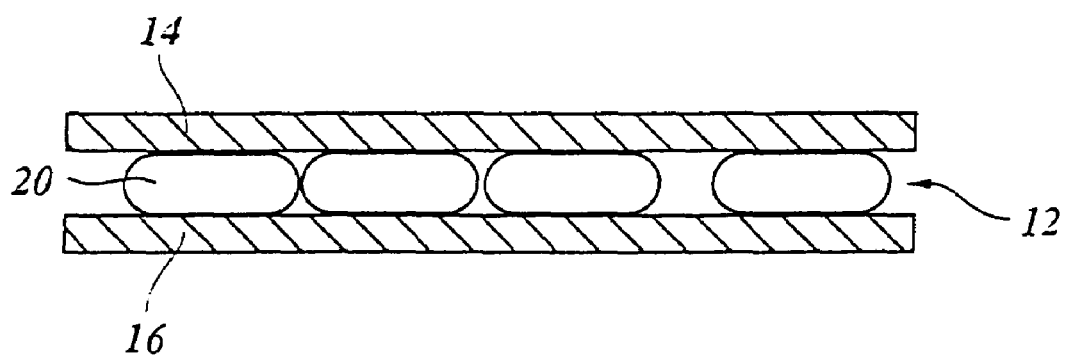

This process is shown in FIGS. 2 to 4. FIG. 2 corresponds roughly to the situation in FIG. 1, in which the culture medium can freely circulate throughout the sample volume 12 and the cells 20 can also move about freely. The thickness d is decreased by means of the actuator 34, shown in FIG. 3, until a situation shown in FIG. 4 is reached, where the cells are markedly flattened by the pressure exerted by the windows 14, 16. Since the imaging of the cells 20 is continually controlled by the image processing system 30, the latter, upon detecting flattening, sends a signal to the control unit 32, which drives the actuator 34 in the opposite direction in order to regain separation value D of FIG. 3, in which the windows 14, 16 have just made contact with the cells 20 without flattening them. This separation D is an optimum value for analyzing the cells 20 and thus the image obtained in FIG. 3 can be employed in the analysis of various cell parameters, such as concentration, size, morphology and vitality.

Figure 5:
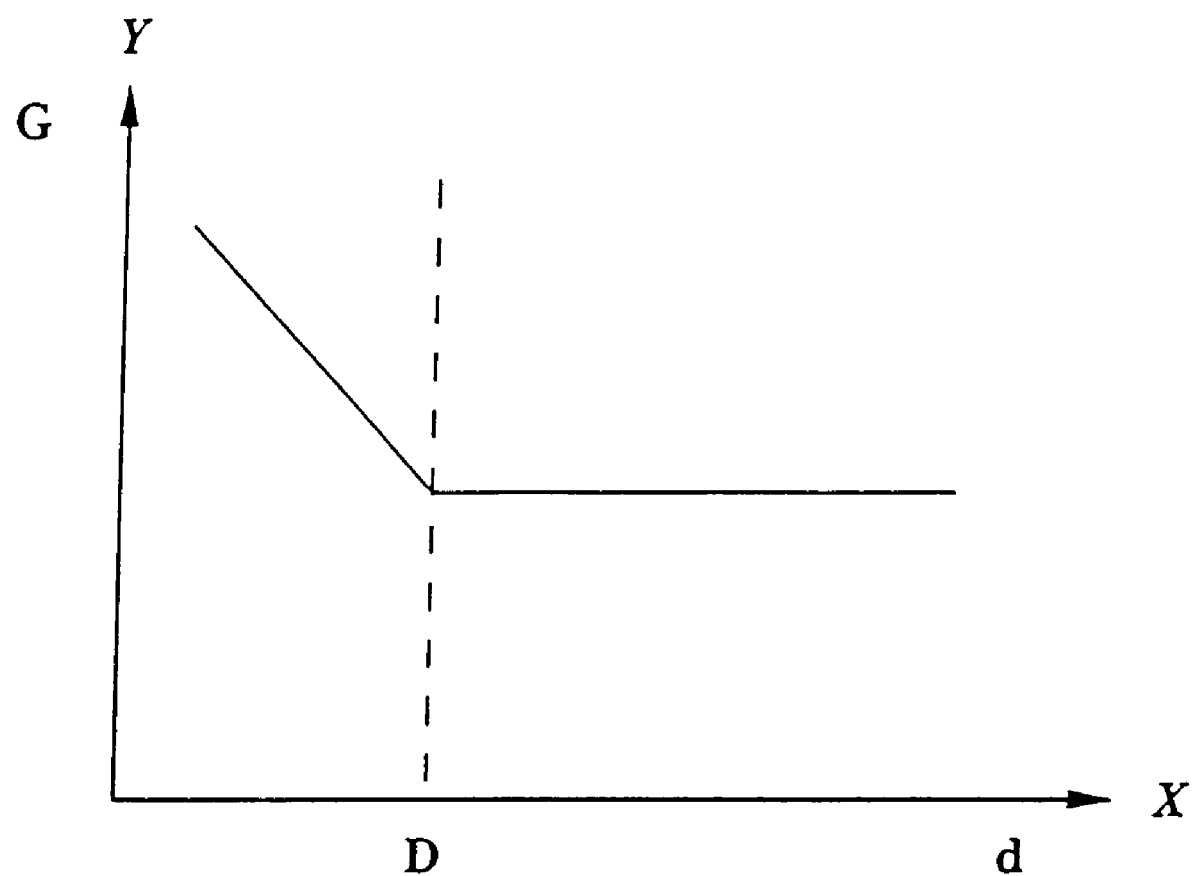
FIG. 5 illustrate a diagram illustrating image size as a function of the thickness of the sample volume.

FIG. 5 illustrates by means of a diagram the process of successively decreasing the thickness d of the sample volume 12. Here the diameter G in the image of a single cell 20 is plotted according to the separation d of the windows 14, 16. If an initially large separation d is gradually decreased, the apparent cell diameter G remains constant at first until the cells 20 are finally clamped between the windows 14, 16 as shown in FIG. 3. At this point, which corresponds to the separation value D, the diameter G starts to increase dramatically as the separation d decreases. Since the parameter G is permanently monitored by the image processing system 30 as the window 16 is moved, this point can be exactly determined so that the thickness d can be precisely set to the separation value D where the flattening process just starts to commence. If this point is overshot, making flattening already measurable, and the separation value D is undershot, the control unit 32 can increase the distance variable d until a situation is reached where d=D.

The point where flattening commences can be stored by the image processing system 30 and must therefore not be determined at the start of each new measuring cycle but can be retrieved from storage for the immediate setting of the separation value D, thus shortening the measuring cycle.

Figure 6:
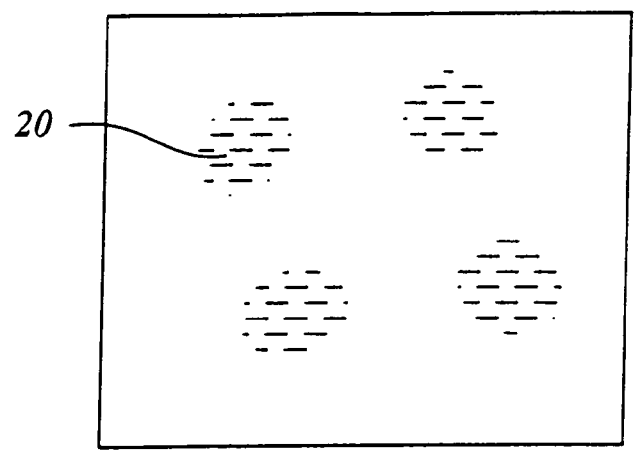
FIGS. 6 to 8 are illustrations of the sample volume pursuant to FIGS. 2 to 4.
Figure 7:
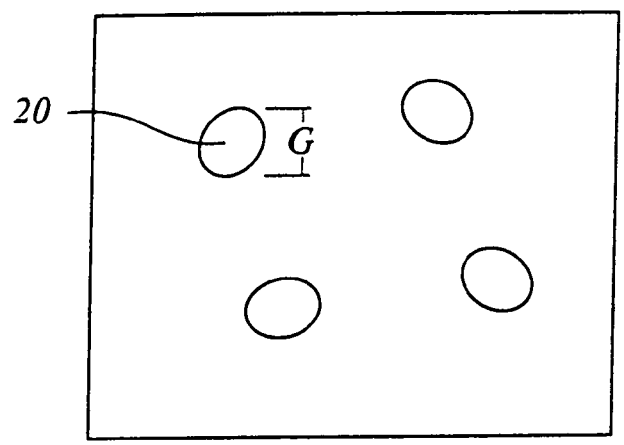
Figure 8:
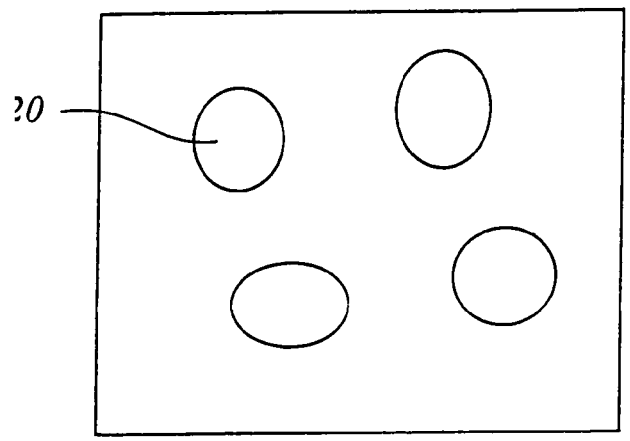

FIGS. 6 to 8 show images of cells 20 recorded by the image sensor 28 and processed by the image processing system 30 in such a manner that the individual FIGS. 5 to 7 can be assigned to FIGS. 2 to 4. FIG. 5 shows merely an unfocussed image of the cells 20, as they are located outside the level of sharp focus of the lens 18. Once the separation distance D is attained, at which point a layer of cells 20 lie exactly between the windows 14, 16, then all cells 20 are located in the level of sharp focus and are imaged clearly. In this situation an optimum analysis of individual cell parameters can be conducted. Furthermore, if the windows 14, 16 are brought closer together, the cells are flattened, as clearly shown in FIG. 7. The diameter G increases and this increase can be detected by a image processing system 30 that has been appropriately programmed, so that the depth d of the sample volume 12 can be set in the manner described above.

Figure 9:
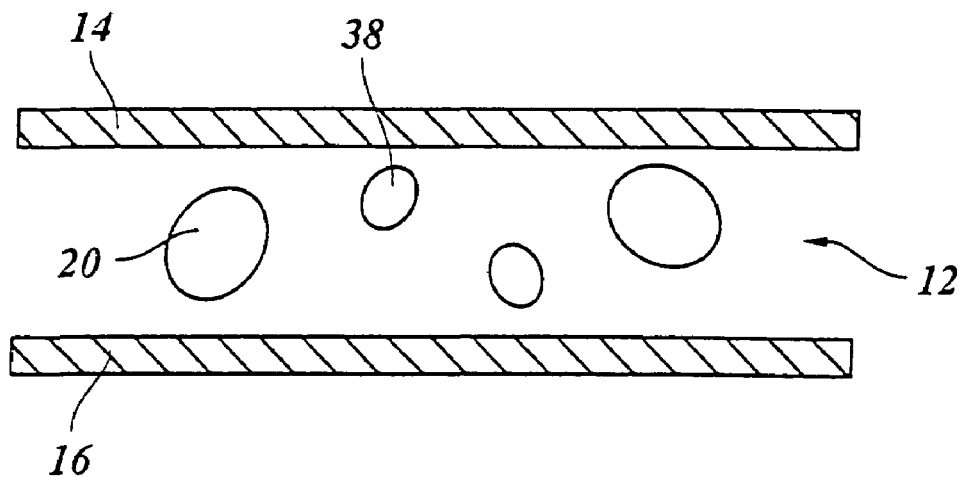
FIGS. 9 to 11 illustrate the sample volume corresponding to FIGS. 2 to 4 with cells of different sizes.
Figure 10:
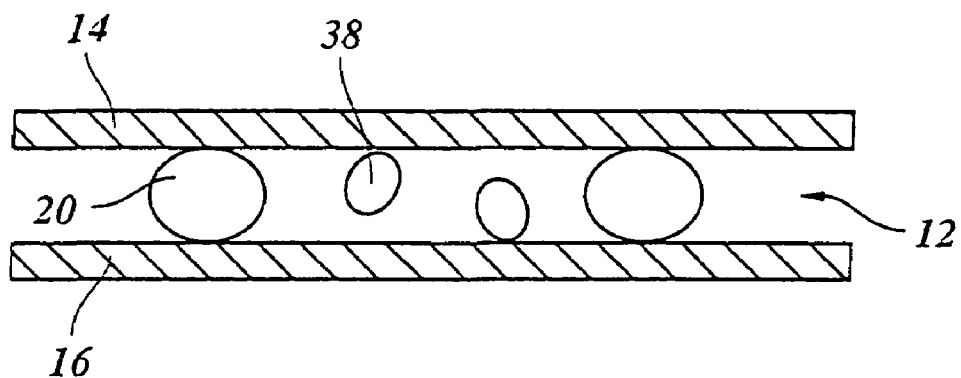
Figure 11:
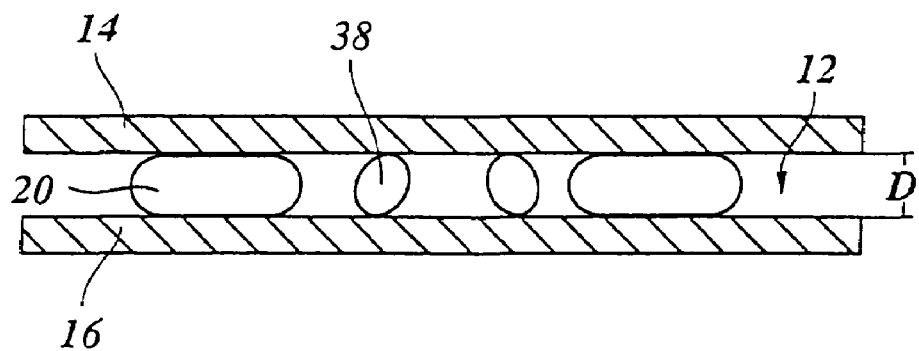

FIGS. 9 to 11 correspond to FIGS. 2 to 4 except that now cells 20, 38 of different sizes are present in the sample volume 12. In this case, cells 38 of a predetermined size can be used to set the separation value D of the windows 14, 16 such that the windows 14, 16 are brought together until the separation distance D is reached where a flattening of the cells 38 of the selected size occurs. The remaining cells 20 are disregarded here. If smaller cells 38 are used in the above example for setting the distance D, the larger cells 20 are naturally flattened to a very significant degree until they reach a state shown in FIG. 11. A severe deformation or even destruction of the larger cells 20 can be accepted in this case, since the image processing system can easily distinguish these cells from the cells 38 to be analyzed. For example, the destroyed cells 20 are simply subtracted from the examined region of imaging. It is also possible to include the larger cells 20 when setting the distance so that the windows 14, 16 are only brought together to the point where a flattening of the larger cells 20 commences. This is the approximate situation shown in FIG. 10.

Figure 12:
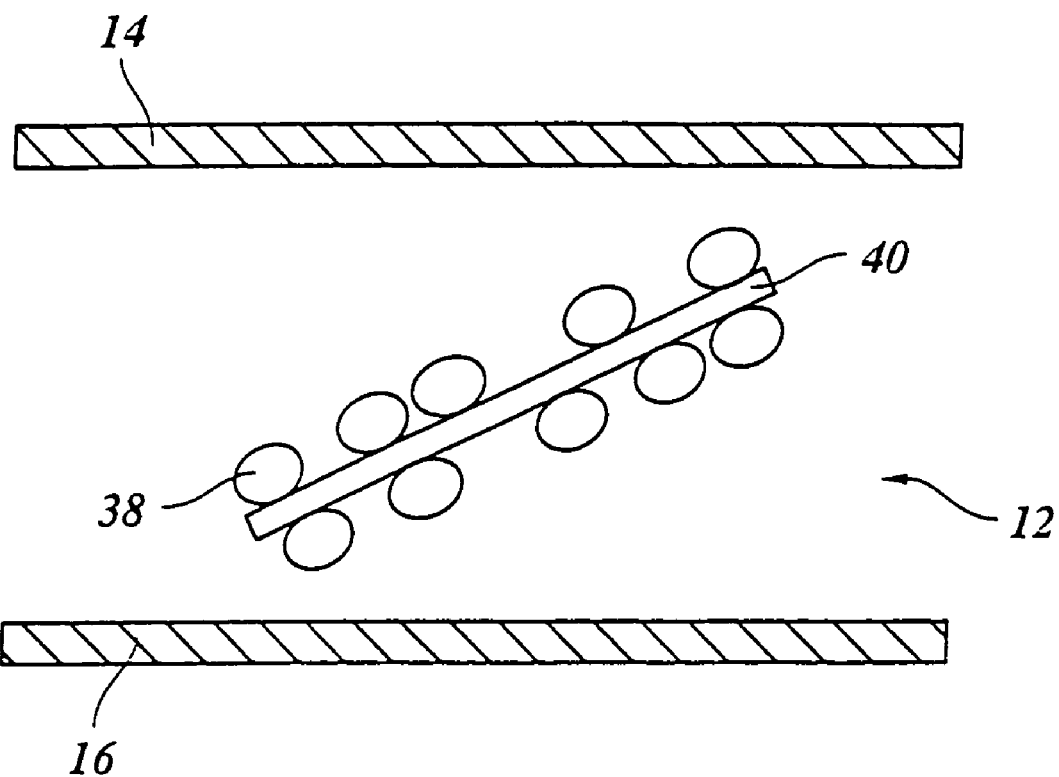
FIGS. 12 and 13 illustrate the sample volume with a carrier.
Figure 13:
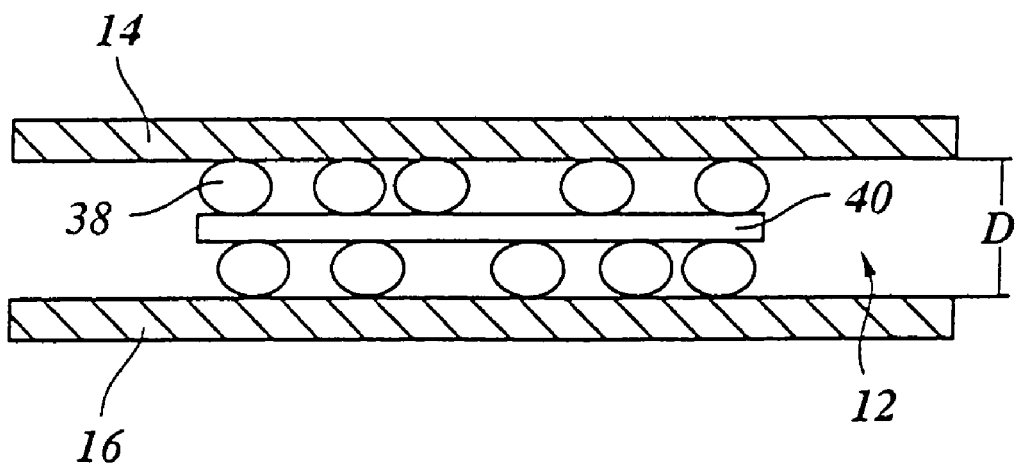

FIG. 12 shows a sample volume 12 having a free-floating carrier 40 and a number of cells 38 adhering to it. The carrier 40 involves polystyrene platelets having a diameter of 0.1 to 0.2 mm and a thickness of 20 µm. Thickness d is reduced in order to observe the adherent cells 38 so that the carrier 40 pursuant to FIG. 13 is flat in its orientation between the windows 14, 16 and the cells 38 on the opposing surface sides are flattened by the surface pressure. But in this case, due to the adhesion of cells 38 on both sides of the surface of the carrier 40, two layers of cells 38 are located in the sample volume 12. In order to examine the cells 38 it is therefore necessary to select a low focus depth of the lens and to displace the object level, i.e. the region of sharp focus by the lens 18, to one of the cell layers. In this case, therefore, the cell layer facing the lens or the cell layer located at the back side of the carrier 40 is selected and imaged. This is achieved by a corresponding adjustment of the microscope lens 18 or of the image sensor 28. Proper depth of field can be achieved by enlarging the numeric aperture and opening the diaphragm 36 so that the cell layer lying in front of or behind the image cell layer does not interfere with imaging. The process of setting the thickness of the sample volume 12 essentially corresponds to the case described above, but differs in that the cells 38 do not lie directly between the windows 14, 16 but rather between one of the windows 14, 16 and the carrier 40. At the point of initial flattening of the cells 38 the distance D of the windows 14, 16 is approximately that of the thickness of the carrier 40 plus the double value of the cell diameter. By virtue of this procedure it is possible, for example to determine quite easily the fouling density and the degree of intergrowth of the cells 38 on the carriers.

Figure 14:
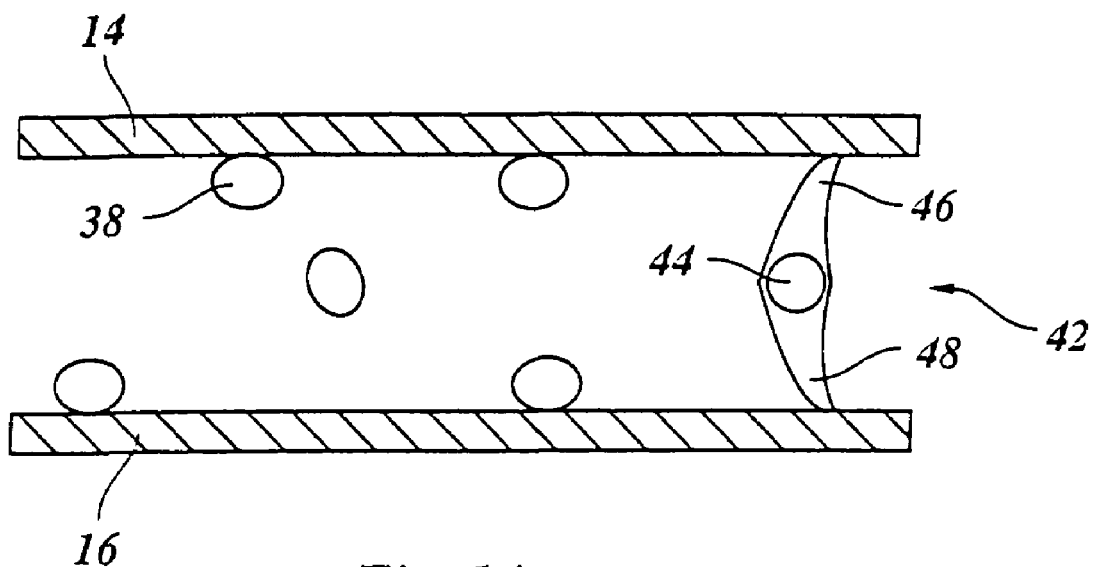
FIGS. 14 and 15 illustrate the sample volume with a wiper.
Figure 15:
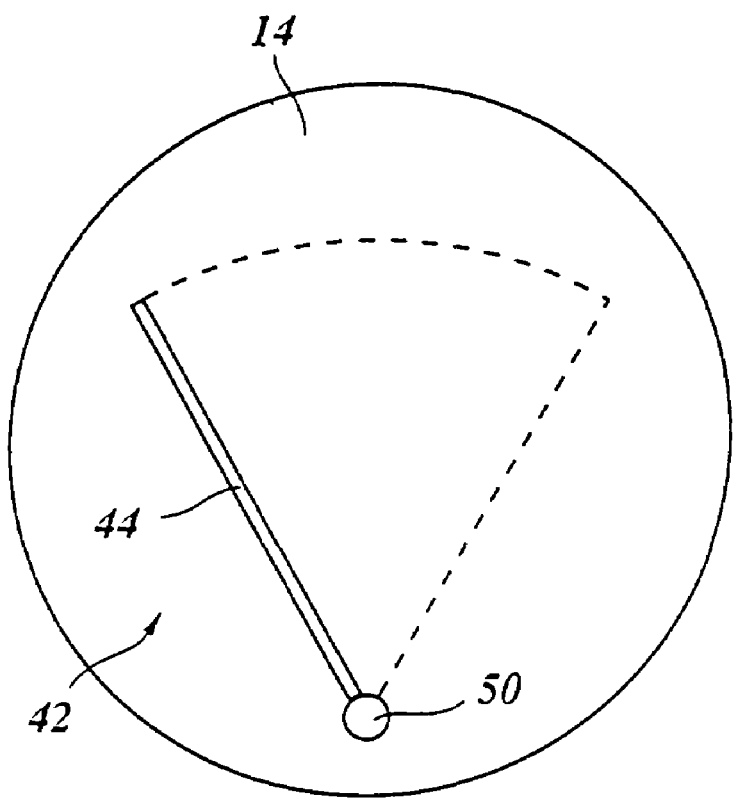

FIG. 14 shows a sample volume 12 with a wiper 42 that removes cells clinging to the windows 14, 16 after the measuring process. This is advantageous because the adherent cells 38 are recorded again in every new measuring cycle and thus distort the obtained results. The wiper 42 is essentially an arm 44 with two opposing rubber lips 46, 48, made of silicone rubber, that abut the windows 14, 16. As shown in FIG. 15, this arm 44 is attached at one end to a pivotal axis 50 which moves it back and forth between the windows 14, 16, thus drawing the rubber lips 46, 48 across the surfaces to clean the windows 14, 16. The image processing system 30 can be programmed to check the efficiency of the wiping action and to repeat it if necessary.

In case the culture medium contains free-floating cells as well as carriers 40, the image processing system 30 can make an assessment based on the image as to whether a carrier 40 or merely free-floating cells are suspended in the sample volume and can then set the separation value D according to the pre-stored values for each of these two cases.

The invention claimed is:

1. A method for the examination of cells (20, 38) in a culture medium for in-situ microscopy in a bio-reactor comprising a microscope with an optical axis, whereby cells in a sample volume (12), said sample volume having a depth that is defined by the depth of field of the microscope (18) lens are microscopically imaged and are automatically recorded and processed by means of an image processing system (30), comprising the steps of adjusting the depth of the sample volume (12) to the size of the cells (20, 38) by successively reducing a separation (d) of the windows while an image size (G) of the cells is simultaneously verified by the image processing system (30) in a manner that a separation value (D) is determined at which the image size (G) of the cells begins to grow, thus corresponding to flattening caused by the contact pressure of the windows (14, 16), and setting the separation (d) of the windows (14, 16) to said separation value (D) for the examination.

2. Method according to claim 1, wherein the image processing system (30) classifies cells (20, 38) into different size categories and determines the separation value (D) as that point where the image size (G) of the cells (20, 38) of a particular size category begins to grow, and that the separation (d) is set to this separation value (D) for the examination.

3. Method according to claim 1, wherein the cells (38) to be examined are adhered to platelet-shaped carriers (40), the separation value (D) is determined where the image size (G) of the cells (38) on a surface side of a carrier lying flat between the windows (14, 16) begins to grow, and the separation (d) is set to this separation value (D) for the examination.

4. Method according to claim 3, wherein, for the examination of cells (38) on a particular surface side of the carrier (40), the object level of a microscope lens (18) to be imaged is shifted to the cell layer, with the depth of field selected such that exclusively cells (38) lying immediately in the object layer are recorded by the image processing system (30).

5. Method according to claim 4, wherein the depth of field is altered by adjusting the numeric aperture of the microscope lens (18).

6. Method according to claim 1, wherein the separation value (D) determined in one measuring cycle is stored and in the subsequent measuring cycles the separation (d) of the windows (14, 16) is set immediately to the stored value (D).

7. Method according to claim 6, wherein the image processing system (30) determines whether a carrier (40) or a cell (20, 38) is present in the sample volume (12), and that on the basis of this assessment the separation (d) of the windows (14, 16) is set to a stored separation value (D) for a carrier (40) or for a cell (20, 38).

8. Method according to claim 1, wherein at least one of the windows (14, 16) is cleaned by a wiper (42) before or after a measurement is made.

9. An apparatus for the examination of cells (20, 38) in a culture medium for in-situ microscopy in a bio-reactor, with a microscope (18) for the imaging of cells (20, 38) within a sample volume (12) having a depth which is defined by the depth of field of the microscope (18) lens, and an image processing system (30) for recording and processing the microscope image, comprising an actuator (34) for adjusting the separation (d) between the windows (14, 16) of the sample volume (12) along the optical axis which can be controlled by the image processing system (30) by means of a control unit (32) in a manner that the separation (d) between the windows (14, 16) can be set for the examination to a separation value (D) at which point an image size (G) of the cells (14, 16) starts to grow in accordance with their flattening caused by the contact pressure of the windows (14, 16).

10. Apparatus according to claim 9, wherein the image processing system (30) is provided for the storage of the determined separation value (D), which can be retrieved for setting the separation (d) to a particular separation value (D).

11. Apparatus according to claim 10, further comprising a diaphragm (36) for setting the depth of field of the microscope.

12. Apparatus according to claim 10, further comprising a wiper (42) for cleaning the windows (14, 16) of the sample volume (12).

13. Method according to claim 3, wherein the separation value (D) determined in one measuring cycle is stored and in the subsequent measuring cycles the separation (d) of the windows (14, 16) is set immediately to the stored value (D).

14. Method according to claim 13, wherein the image processing system (30) determines whether a carrier (40) or a cell (20, 38) is present in the sample volume (12), and that on the basis of this assessment the separation (d) of the windows (14, 16) is set to a stored separation value (D) for a carrier (40) or for a cell (20, 38).

15. Method according to claim 13, wherein at least one of the windows (14, 16) is cleaned by a wiper (42) before or after a measurement is made.

16. Method according to claim 14, wherein at least one of the windows (14, 16) is cleaned by a wiper (42) before or after a measurement is made.

17. Apparatus according to claim 11, further comprising a wiper (42) for cleaning the windows (14, 16) of the sample volume (12).

* * * * *